US006464673B1

(12) United States Patent
Ben Natan

(10) Patent No.: US 6,464,673 B1
(45) Date of Patent: Oct. 15, 2002

(54) ANTI-IRRITANT DISPOSABLE DIAPER

(76) Inventor: Chaim Ben Natan, Shikunim Hadashim 86, Kfar Chabad (IL), 72915

( * ) Notice: Subject to any disclaimer, the term of this patent is extended or adjusted under 35 U.S.C. 154(b) by 97 days.

(21) Appl. No.: 09/662,163

(22) Filed: Sep. 14, 2000

(30) Foreign Application Priority Data

Sep. 16, 1999 (IL) .................................... 131926

(51) Int. Cl.$^7$ ................................................ A61F 13/15
(52) U.S. Cl. ..................... 604/385.01; 604/317
(58) Field of Search .......................... 604/317, 322, 604/338, 326, 327, 339, 353, 354, 355, 356, 380; 2/400–406

(56) References Cited

U.S. PATENT DOCUMENTS

| 976,883 A | * | 11/1910 | Keagy |
| 2,796,865 A | * | 6/1957 | Reinhardt |
| 2,837,095 A | * | 6/1958 | Stevenson |
| 3,424,160 A | * | 1/1969 | Koornwinder et al. |
| 5,586,978 A | * | 12/1996 | Bayne |
| 6,293,937 B2 | * | 9/2001 | Matsushita et al. |

FOREIGN PATENT DOCUMENTS

GB        2150835 A   *   7/1985

* cited by examiner

*Primary Examiner*—Jeanette Chapman
(74) *Attorney, Agent, or Firm*—Edward Langer

(57) ABSTRACT

An anti-irritant disposable diaper to contain solid waste and maintain it and wet absorbent material apart from the skin of the infant, thus removing the two major sources of irritation caused by prior art disposable diapers. The diaper comprises a front portion, a crotch area, a rear portion, and closing arrangement. A rib extending from the top edge of the diaper to the top rear edge of the diaper maintains a gap between the diaper and the skin surface. A solid waste receptacle is retained in the crotch area of the diaper interior, and may comprise a bag attached either to a set of straps, or directly to the sides of the crotch area of the diaper, or to an aperture provided in the diaper. Alternatively, the rigid rib may be provided with a rigid pocket for solid waste containment.

21 Claims, 13 Drawing Sheets

ANTI-IRRITANT DISPOSABLE DIAPER

FIELD OF THE INVENTION

The present invention relates to disposable diapers, in particular to diapers constructed for protection from skin irritation.

BACKGROUND OF THE INVENTION

Use of disposable diapers has provided a convenient and sanitary solution for parents of infants. However, the plastic coating used on the outside of the absorbent layers, while helping to prevent leaks, also causes the waste to be left on the skin of the infant, and creates a breeding ground for rash-causing micro-organisms.

Many advances have been made in diaper technology such as the use of gels to lock in liquid waste and prevent it from irritating the infant's skin. These advances have improved the use of disposable diapers. However, many infants continue to suffer from irritations and rashes. A less apparent problem is those rashes caused by contact with solid waste.

Additionally, disposable diapers can be expensive to use and are perceived as wasteful. Dirty diapers must be changed as soon as possible so as to prevent rashes, but often the diaper is not wet and its absorbent capacities have not been realized. Because disposable diapers are not biodegradable, it is necessary to find ways of conserving the use of diapers.

SUMMARY OF THE INVENTION

The present invention overcomes the problems associated with the prior art by providing an anti-irritant disposable diaper construction which contains solid waste and distances the surface of the absorbent material from the skin of the infant.

The present invention provides a sanitary device, typically a diaper or sanitary garment or the like, that contains solid waste, so as to prevent its coming in contact with the skin of the infant, so as not to cause rashes. This also makes cleaning the infant easier, during the diaper changing process. Additionally, the sanitary device is designed to keep liquid waste distanced from the skin of the wearer. These sanitary devices are also economical to use as they may be used multiple times.

In one embodiment of the present invention there is provided an anti-irritant disposable diaper comprising a front portion, a crotch area, a rear portion, a closing mechanism, a substantially rigid element extending from the top front edge of the diaper, along the crotch area, to the top rear edge of the diaper for maintaining a gap between the diaper and the skin surface, and a solid waste containment means retained in the gap.

In this embodiment, the diaper is provided with a substantially rigid rib extending along its length from the top front to the top back of the diaper. The rib is rigid enough to hold its distinctive shape while not causing discomfort or injury to the infant. The rib is provided with a distinctive shape which distances the inner surface of the diaper from the skin of the infant. The rib is of a width of up to approximately 4.5 cm, which is the width of a conventional diaper at the crotch when worn. The rigid rib develops a gap of approximately 5 cm between the skin of the infant and the diaper. This gap functions both to keep the wet surface of the diaper from coming in contact with the skin of the infant, and to provide a gap in which the solid waste is maintained.

The sides of the diaper are longer than the conventional diaper so as to provide sufficient coverage, despite the 5 cm gap developed by the rib. When the infant is seated, the bag becomes folded in such a way as to contain the waste.

The rib may be provided as an integral part of the disposable diaper, or may be provided in a multi-use form for attachment to the disposable diaper. The rib may be attached, by way of example, by snaps or other connections or may be inserted in a sleeve contained in the disposable diaper.

In another embodiment, there is further provided a solid waste containment means comprising a disposable diaper with a set of straps for attaching a solid waste containment bag. The straps are constructed from a non-irritating material. The straps are provided extending from the crotch area of the diaper, are wrapped around the infant's legs and are attached by the user to the top of the back of the diaper. The straps may be attached with mechanical fasteners, for example, using Velcro. The solid waste containment bag may then be positioned opposite the anal opening of the infant and attached to the straps at the appropriate location for the infant's anatomy.

The bag may be attached, by way of example, by a set of adhesive strips, providing for a varied width between the straps, dependent on the infant's size. The straps cause the solid waste containment bag to stay in place even if the diaper moves with the infant. Optionally, the solid waste containment bag may be provided with an additional adhesive point so as to allow the bag to be attached to the diaper itself, in the crotch area so that the bag cannot be come twisted or displaced, and therefore close. The width of the rigid rib maintains a gap between the legs so that the solid waste may fall into the solid waste containment bag.

In a case where a diaper is dirty and not wet, it would only be necessary to open the diaper, remove the bag and replace it. This would conserve for reuse a diaper with absorbent padding which has not been used for liquid waste.

Alternatively, the rigid rib is provided with a region of lower rigidity, causing the diaper to become compressed upon the infant's sitting down. The solid waste containment means are provided as a flexible flap extending from the front portion of the crotch area of the diaper and being positioned under the infant so as to cover the solid waste when the infant is sitting down.

In yet another embodiment, the rigid rib is provided with a rigid pocket. The rigid pocket creates a gap under the infant, even when the infant is seated. The solid waste sits in this gap, and is therefore protected from the pressure of the seated infant. The width of the rigid rib is such that the infant is supported by the edges of the rib which surround the rigid pocket.

When the infant is lying down, or sleeping, a separate absorbent pad, such as a diaper doubler, may be added to prevent liquid waste from leaking out because of the gap formed in the diaper.

In an additional preferred embodiment, there is provided a diaper formed with an aperture in which may be affixed a solid waste containment bag. The bag may be attached, by way of example, with Velcro. The lower end of the bag may be attached to the rigid rib in order to prevent the bag from becoming twisted. For aesthetic purposes, an outer covering may be provided to enclose the diaper, rigid rib and waste containment bag. This covering may be provided as an integral part of the diaper or as a separate, reusable unit.

In still another embodiment, there is provided a diaper having sides longer than those of a conventional diaper and further provided with a solid waste containment bag. The sides of bag opening are fixed, by way of example, using Velcro to the sides of the crotch area of the diaper, and the lower end of the bag is attached to the lower inner surface of the crotch area of the diaper to maintain the bag in a fixed, open position while the infant is standing. When the infant sits down, the bag becomes folded in such a way as to contain the waste.

Other features and advantages of the invention will become apparent from the following drawings and descriptions.

BRIEF DESCRIPTION OF THE DRAWINGS

For a better understanding of the invention with regard to the embodiments thereof, reference is made to the accompanying drawings, in which like numerals designate corresponding elements or sections throughout and in which.

DETAILED DESCRIPTION OF THE INVENTIVE EMBODIMENTS

Figure 1:
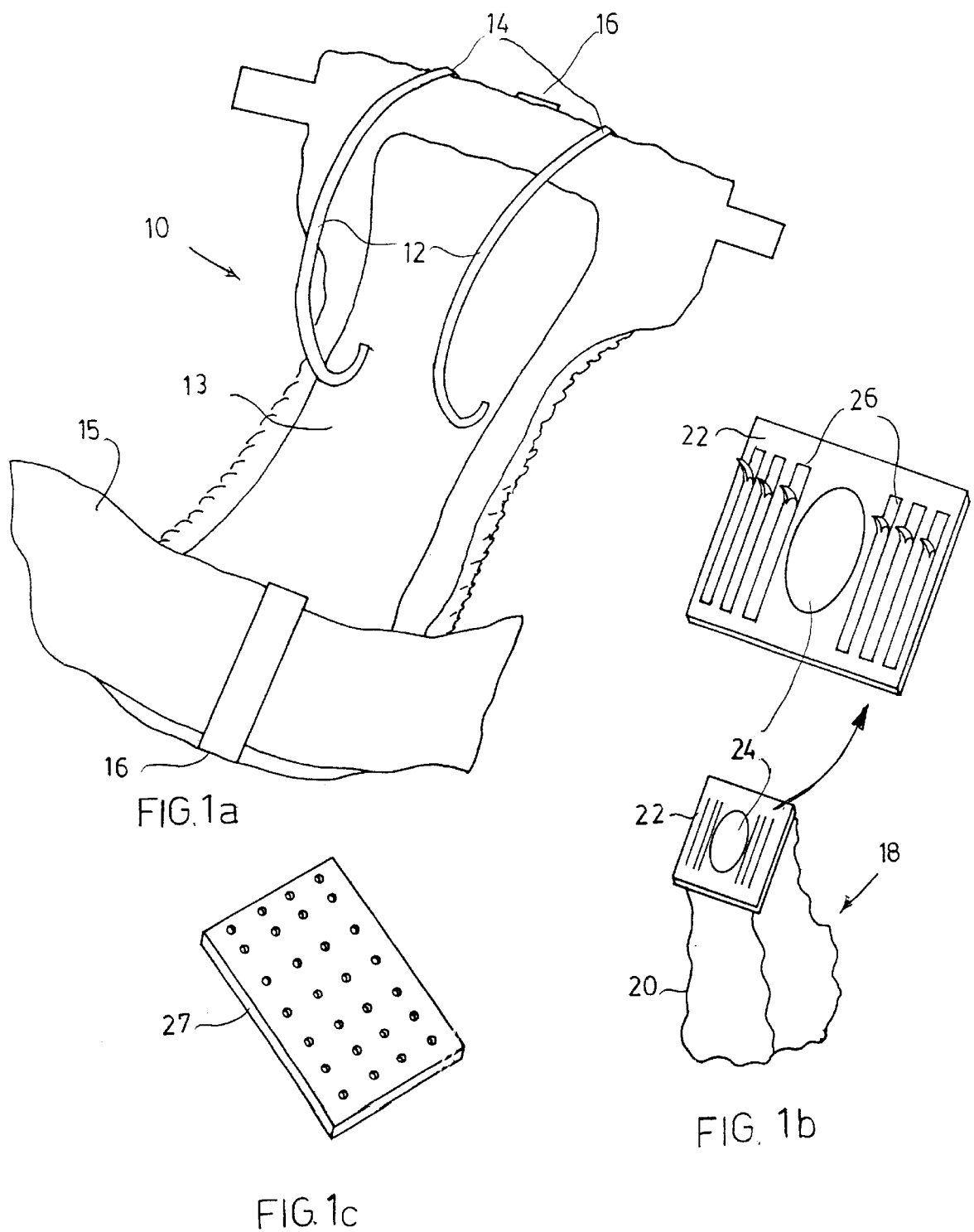
FIGS. 1a–c show a front perspective view of the diaper of the present invention and its component parts.

Referring now to FIG. 1a, there is shown diaper 10 constructed in accordance with the principles of the present invention. Diaper 10 comprises straps 12 which are attached at one end to crotch area 13 of diaper 10 and at the other end are removably attachable at points 14 on the back upper edge of diaper 10. Diaper 10 is additionally provided with substantially rigid rib 16. Rigid rib 16 typically has a width sufficient to provide rigidity, for example, approximately 4.5 cm in width, which is approximately equal to the width of the crotch of a conventional diaper. The rigidity of rib 16 is such that the shape of diaper 10 is maintained but the rib is not injurious or uncomfortable for the child.

In FIG. 1b, a solid waste containment bag 18 is shown which is provided in diaper 10 in accordance with the inventive construction. Bag 18 is comprises receptacle 20 and cover 22. Cover 22 has formed therein an opening 24 through which the solid waste enters receptacle 20, and is provided with exposable adhesive strips 26 for attachment of bag 18 to straps 12. Straps 12 maintain the bag in place even if diaper 10 moves with the infant's motion.

FIG. 1c shows pad 27 which can be placed as needed within diaper 10, providing added absorbency for use when the infant is sleeping so as to prevent leakage of liquid waste.

Figure 2:
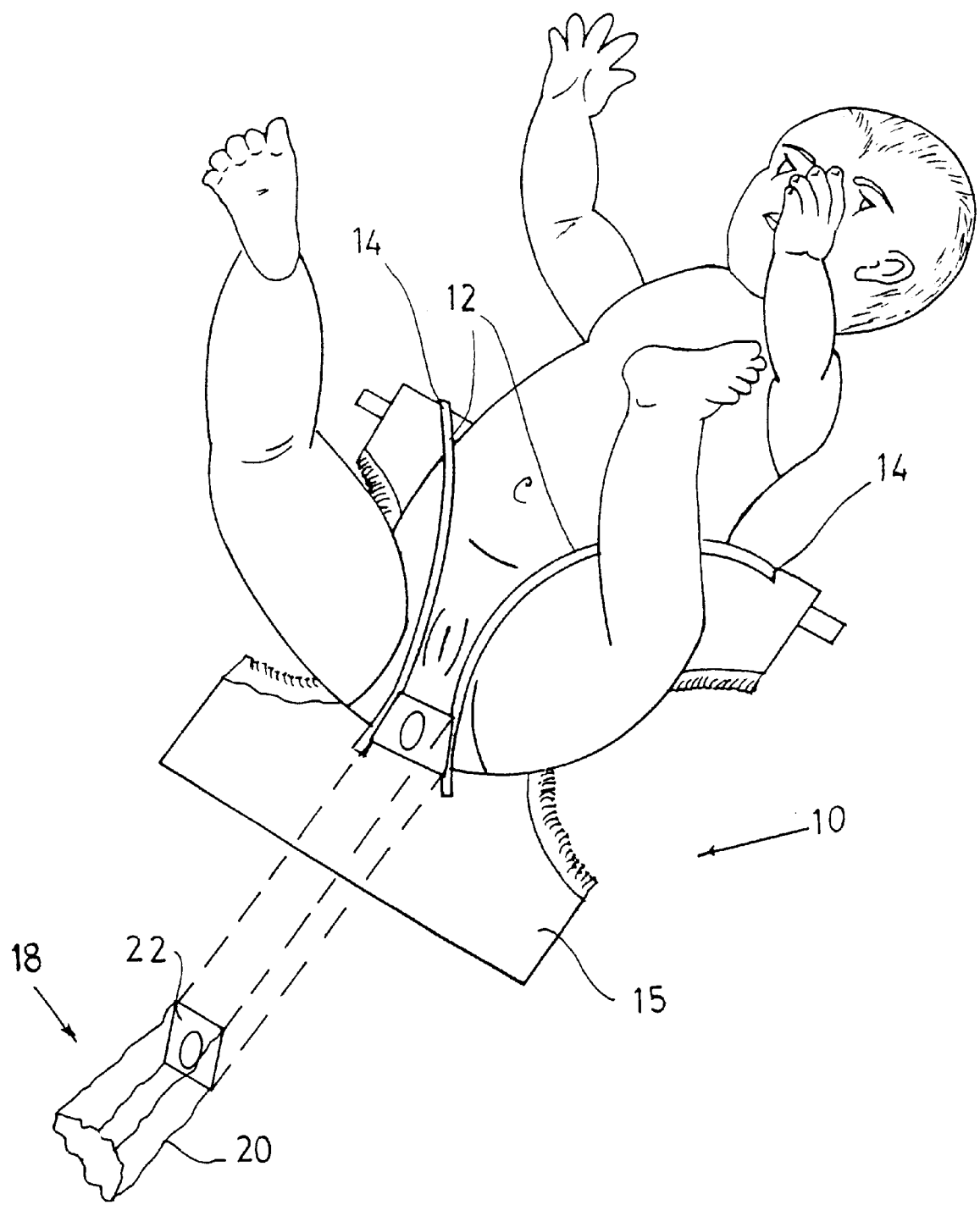
FIG. 2 shows a top view illustrating the method of use of the diaper of the present invention.

Referring now to FIG. 2, there is illustrated a method of using the diaper of the present invention. The infant is placed on open diaper 10 and straps 12 are attached over the infants legs at points 14. Solid waste containment bag 18 is attached to straps 12 by use of adhesive strips 26, at a point which is appropriate to the anatomy of the infant so that hole 24 is opposite the anal opening of the infant. Multiple adhesive strips 26 are provided so that the best fit can be chosen by the user. The approximately 4.5 cm width of rigid rib 16 maintains a gap between the infant's legs to allow the solid waste to pass into solid waste containment bag 18. Optionally, an additional adhesive point (not shown) may be provided at the bottom of receptacle 20, to allow receptacle 20 to be attached to the crotch area of diaper 10 so as to prevent it from becoming twisted or displaced.

Figure 3A:
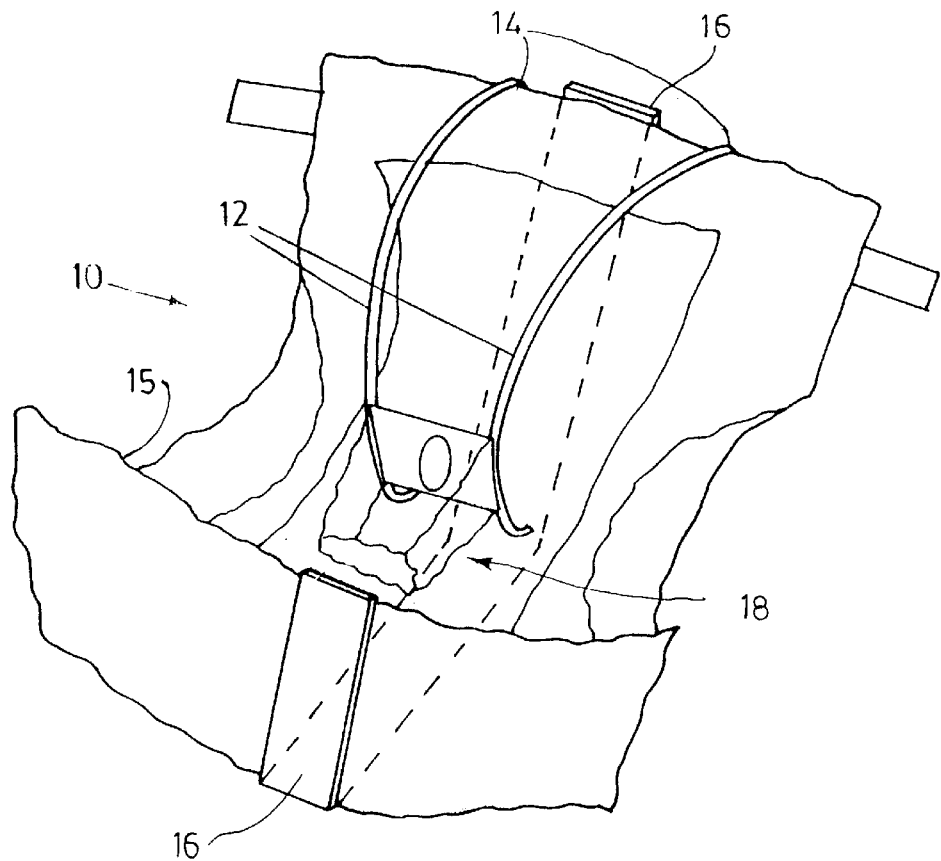
FIGS. 3a–b show a front perspective view and a side perspective view of the diaper of the present invention, respectively.
Figure 3B:
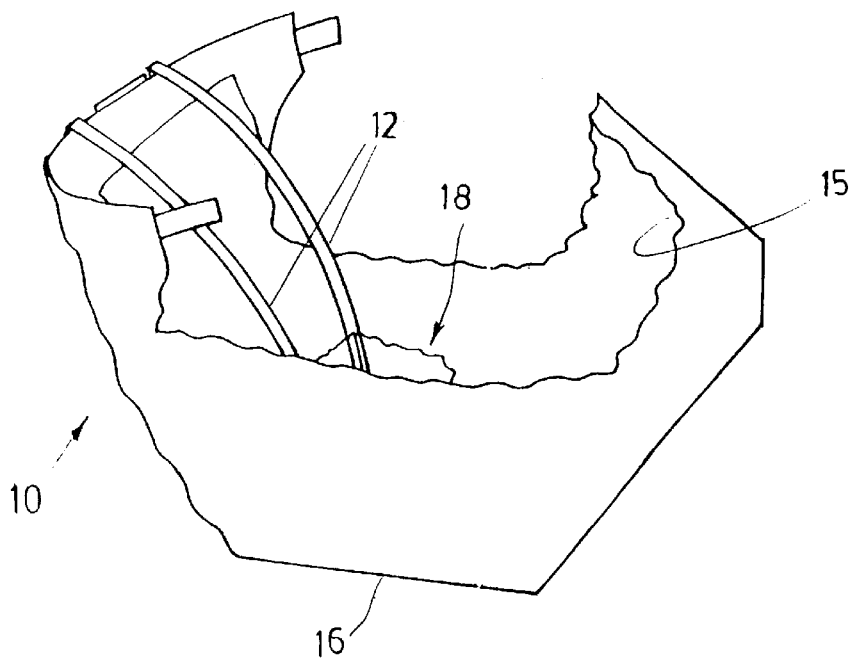

In FIG. 3a, there is shown a front perspective view of diaper 10 with solid waste containment bag 18 attached to straps 12. Rigid rib 16 is formed from a substantially rigid material and holds diaper 10 in a predetermined shape, while not being rigid enough to cause discomfort to the infant. Rib 16 extends from the top front edge of diaper 10, along its length and until the top back edge. This shape is shown more clearly in the side view presented in FIG. 3b. Rigid rib 16 may be an integral part of diaper 10, as shown, or may be provided as a multi-use item which is attached to disposable diaper 10, by way of example, by means of re-openable snaps or inserted in a slot provided for this purpose (not shown).

Figure 4:
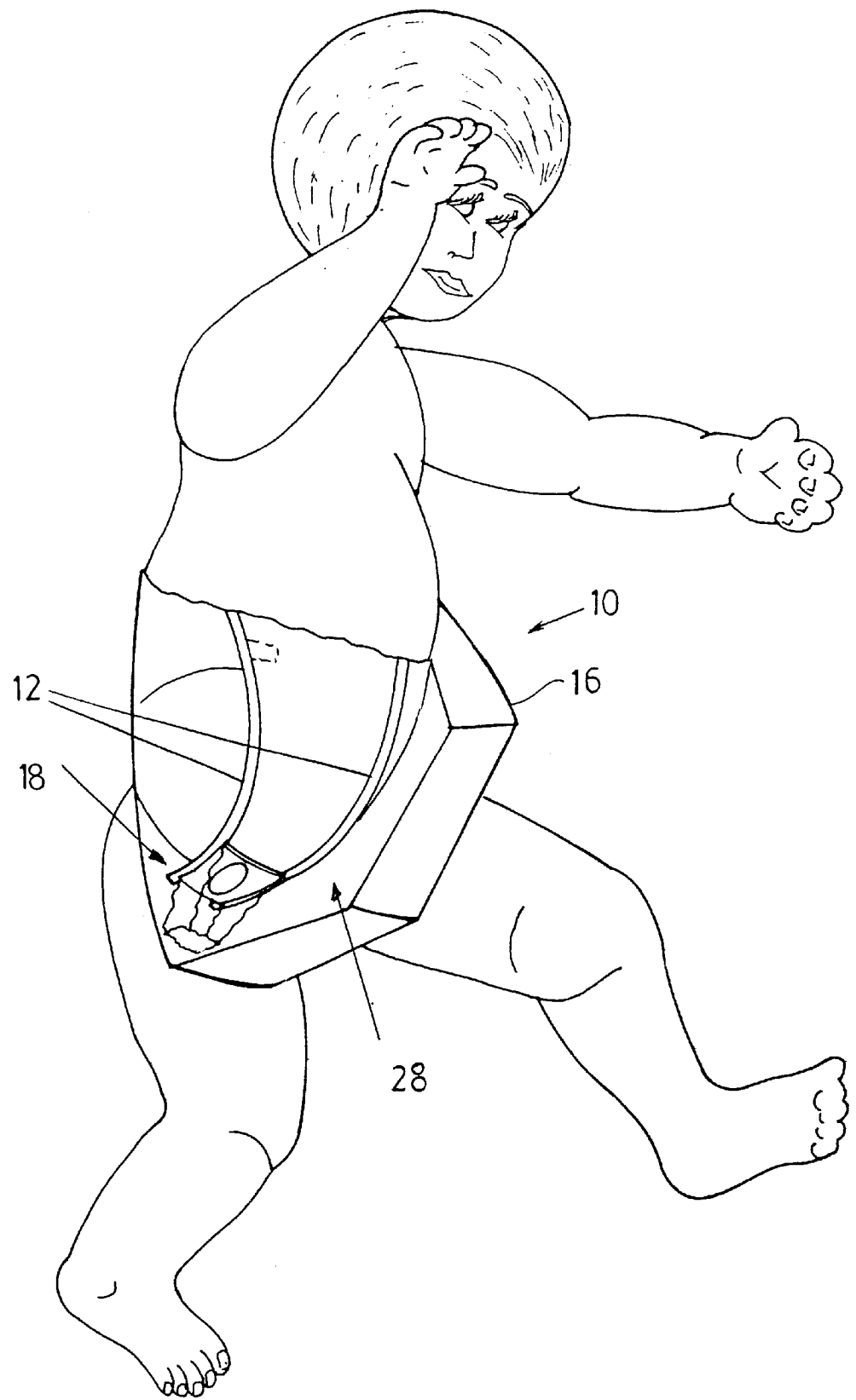
FIG. 4 shows a cross-sectional side view of the diaper of the present invention.
Figure 5:
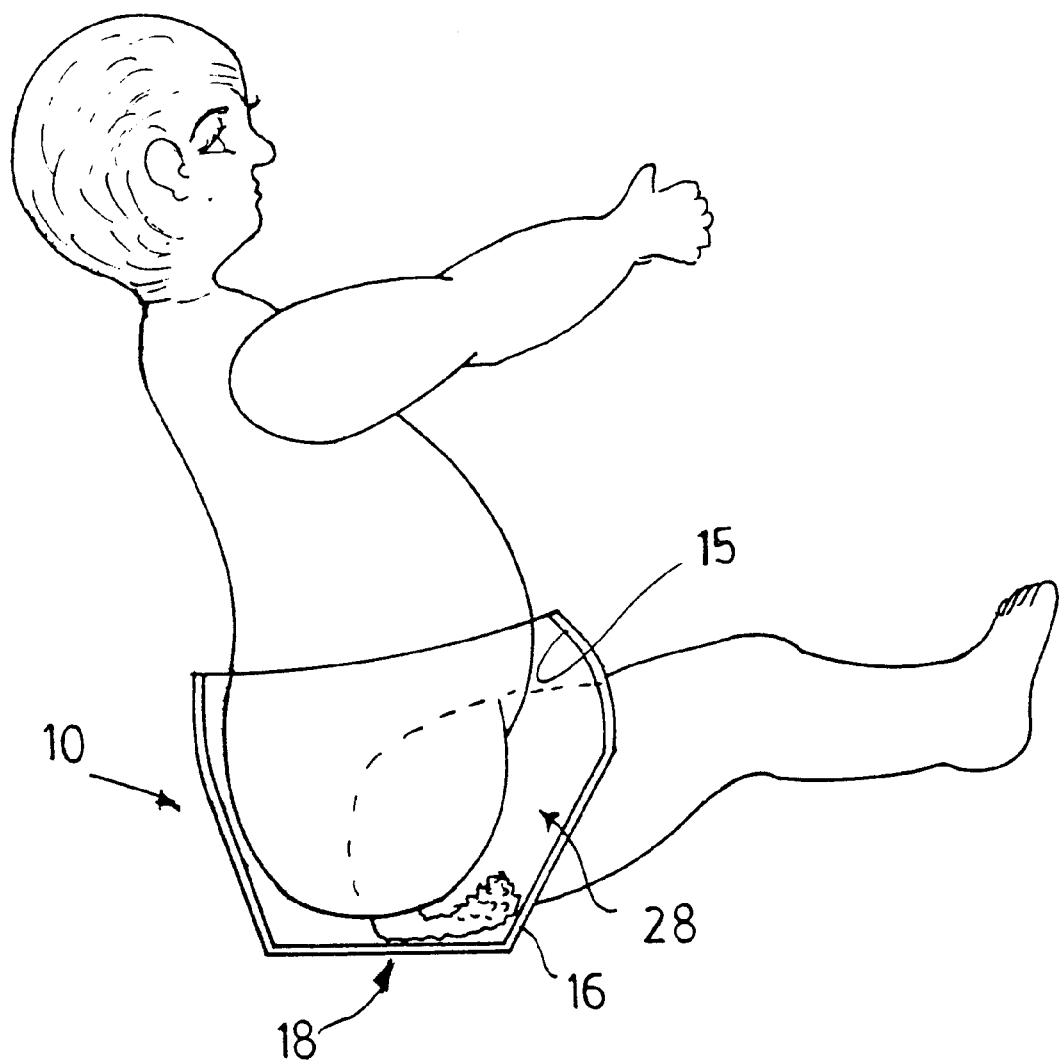
FIG. 5 shows a cross-sectional side view of the diaper when worn in a sitting position.

FIG. 4 shows a cross-sectional side view of the diaper when worn, showing gap 28 developed between diaper 10 and the infant by rib 16. Gap 28 is approximately 5 cm in depth. Solid waste containment bag 18 is disposed in gap 28. When the infant is lying down, pad 27 (see FIG. 1c) may be used for added absorbency so that liquid waste will not pool on the skin of the infant, below the diaper, because of gap 28. When the infant assumes a sitting position, as in FIG. 5, solid waste containment bag 18 becomes folded so as not to allow the pressure of the infant on bag 18 to discharge the contents of receptacle 20.

When bag 18 is used, diaper 10 is opened and bag 18 is removed. It is not necessary to replace the whole diaper 10 if it is unused, rather a new bag 18 may be put in place and diaper 10 reclosed for further use. The improved diaper of the present invention is economical, as it contains solid waste within the solid waste containment bag so that the absorbent material remains clean and may be reused when it is not wet.

Figure 6A:
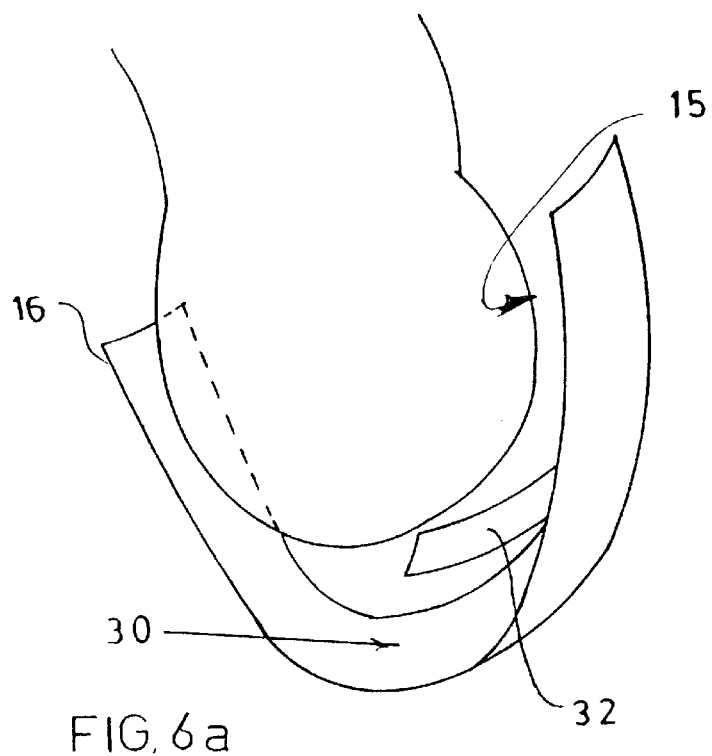
FIG. 6 shows a side view of an alternative embodiment of the diaper of the present invention in which a flexible flap is provided.
Figure 6B:
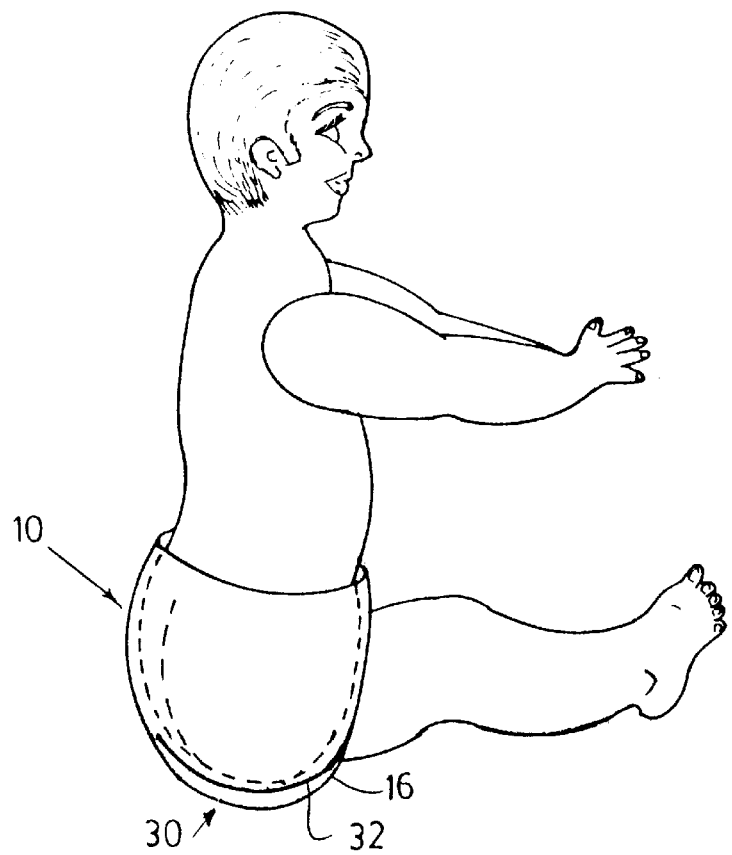

Referring now to FIG. 6a, there is shown an alternative embodiment of the solid waste containment means. In this embodiment, rigid rib 16 is provided with a region 30 of lower rigidity, and a flexible flap 32 is arranged within diaper 10. When the infant assumes a seated position as shown in FIG. 6b, the front area 15 of diaper 10 near the crotch area becomes compressed, pushing it further backwards. Thus, flexible flap 32 moves rearwardly to cover the solid waste when the infant assumes the seated position, thereby protecting the infant's skin from irritation caused by the solid waste.

Figure 7:
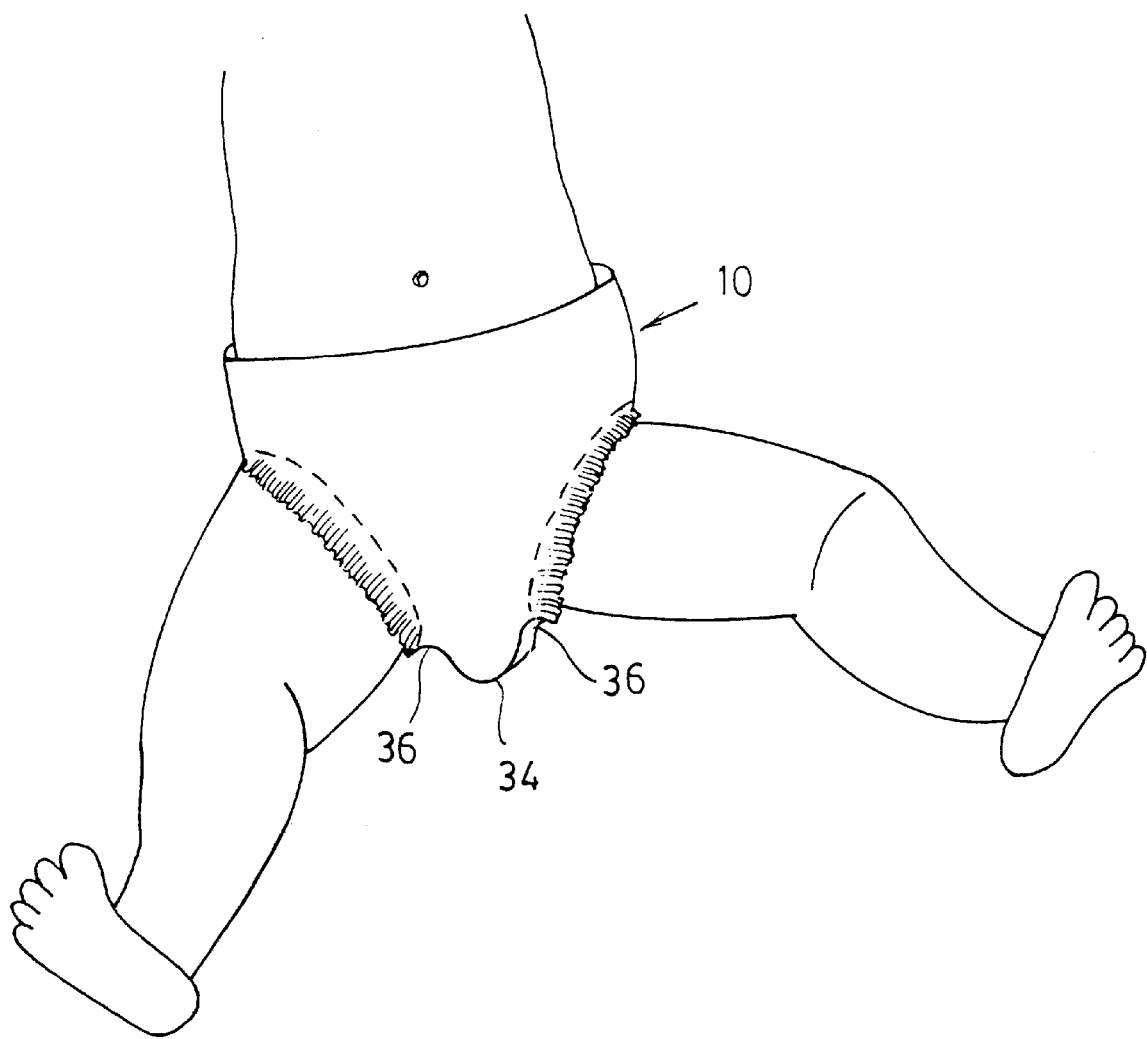
FIG. 7 shows a front view of yet another embodiment of the diaper of the present invention in which a rigid pocket is provided.
Figure 8:
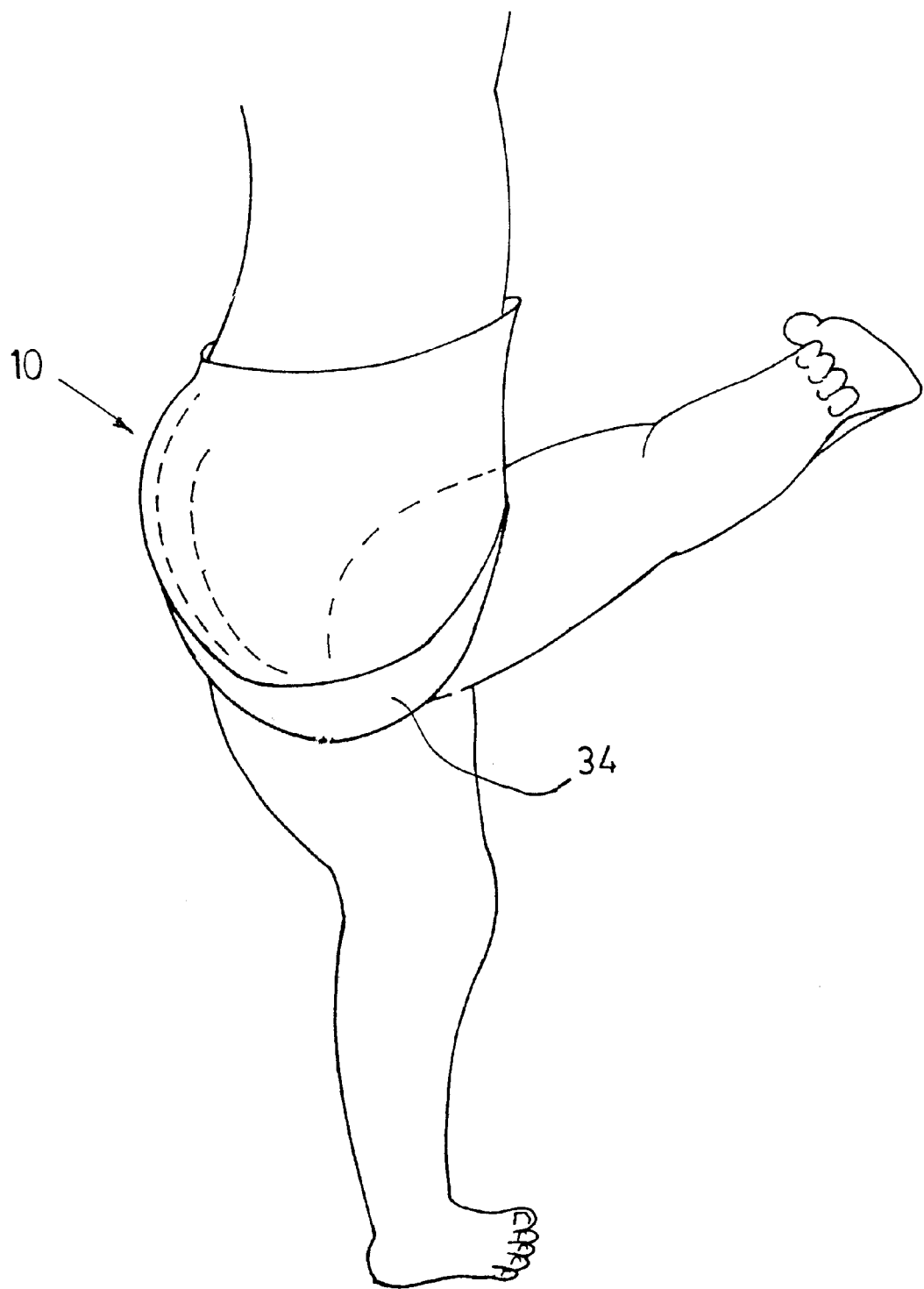
FIG. 8 shows a side view of the rigid pocket.

In FIG. 7, there is shown a further alternative embodiment in which rigid rib 16 (not shown) is formed with rigid pocket 34 for containment of solid waste. Rigid pocket 34 maintains its shape, even under pressure of the seated infant, and thereby protects the infant's skin from coming in contact with the solid waste. Rigid rib 16 is provided with a greater width than rigid pocket 34, so that substantially flat edges 36 of rigid rib 16 provide a support area for the sitting infant. This embodiment may be provided with a solid waste containment bag 18, or it may be arranged without one. FIG. 8 shows a side view of rigid pocket 34.

Figure 9:
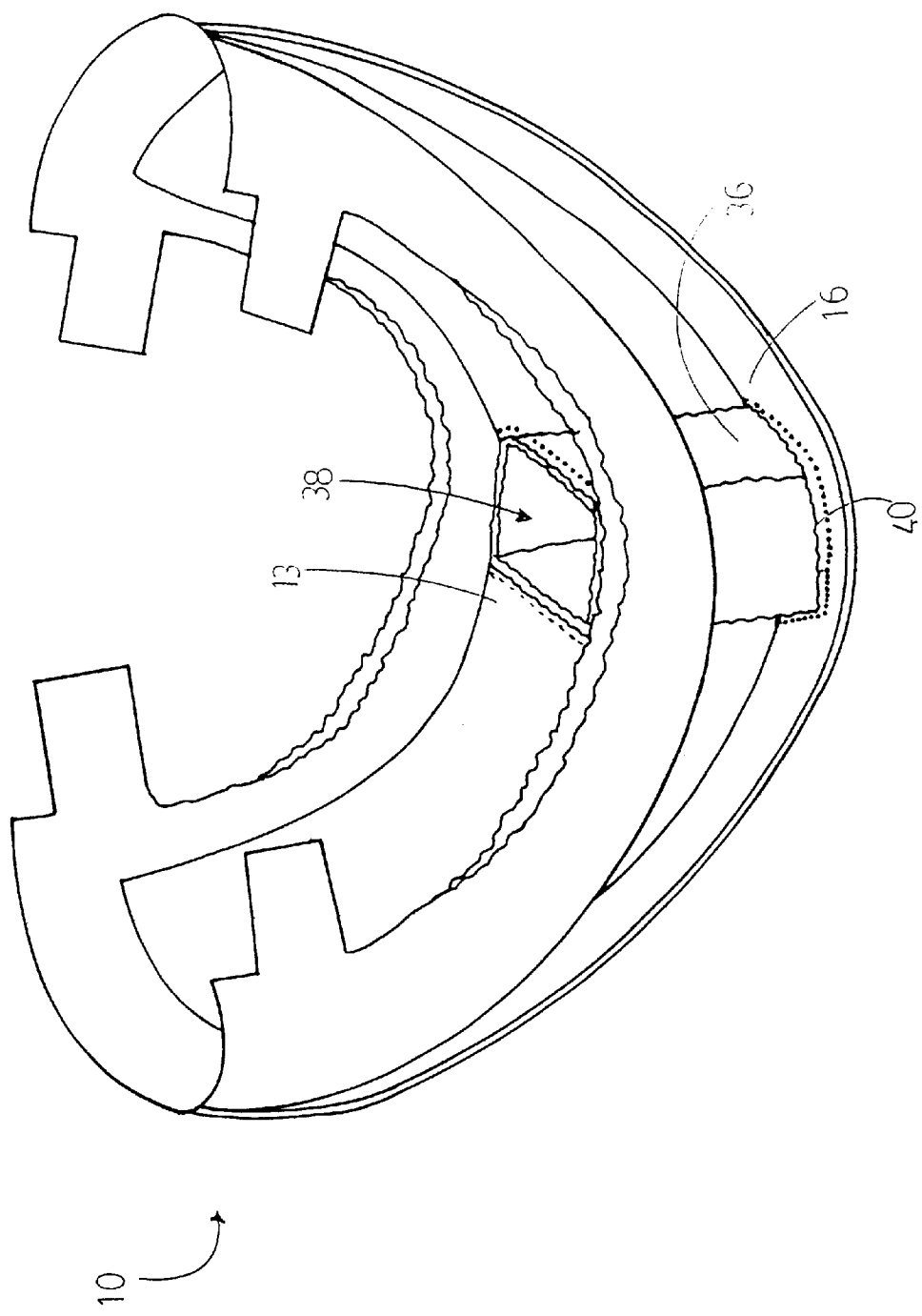
FIG. 9 shows a side perspective view of an alternative embodiment of the present invention provided with an opening in the diaper for insertion of a waste containment bag.

In FIG. 9, there is shown an additional alternative embodiment of the present invention, in which diaper 10 is provided with a removable solid waste containment bag 36, the opening of which is situated in an appropriate aperture 38 formed in crotch area 13 of diaper 10. Bag 36 is attached to diaper 10 by pressing the edge of bag 36 surrounding the opening against an adhesive area provided on diaper 10 around the perimeter of aperture 38. The lower end 40 of bag 36 is attached by adhesive to rib 16, preventing the bag from becoming twisted or displaced. When the infant is seated, the bag 36 becomes folded in such a way as to contain the waste.

Figure 10:
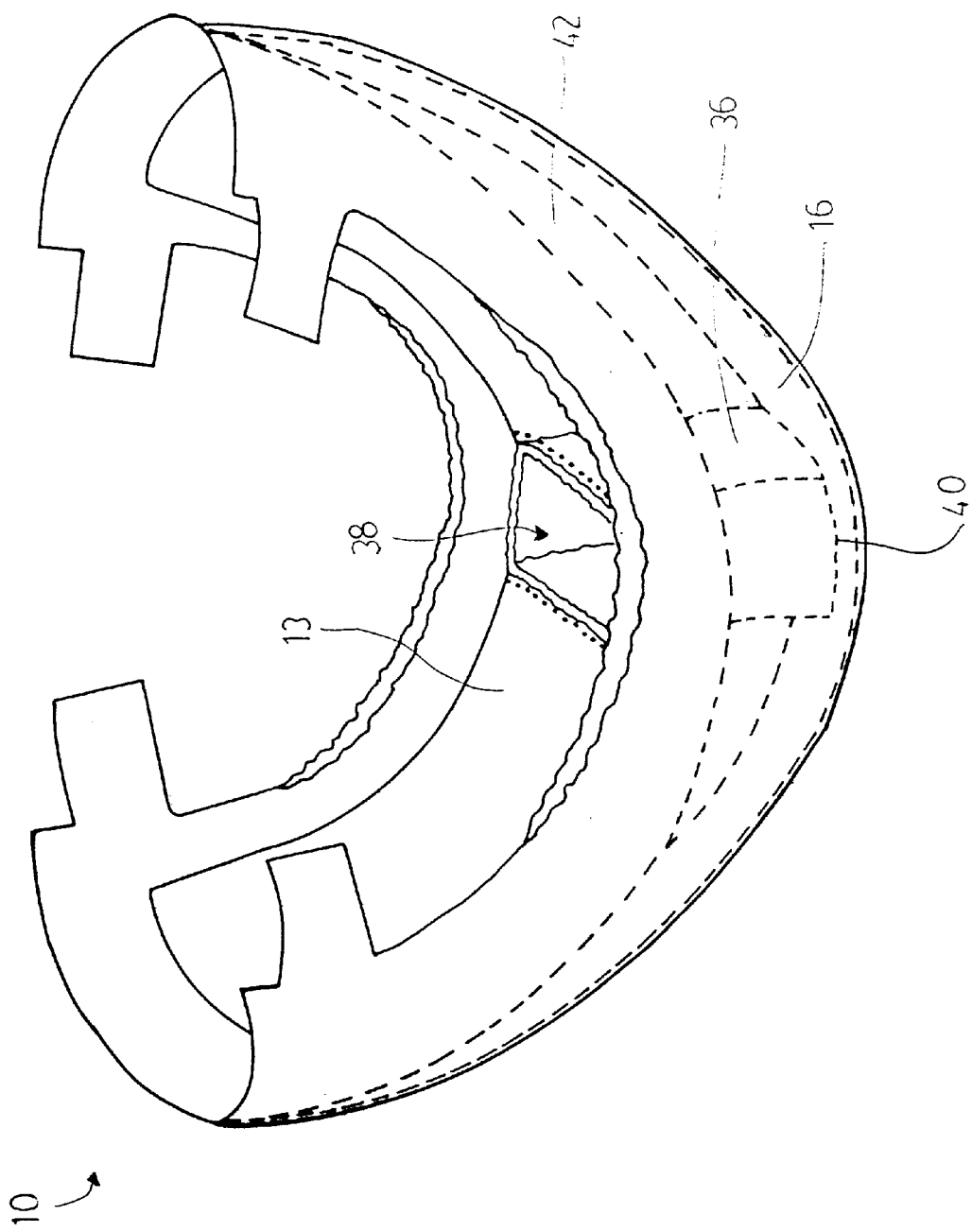
FIG. 10 shows the embodiment of FIG. 9 in which the diaper, rigid strip and waste containment bag are encased in an external covering.

As shown in FIG. 10, an outer covering 42 may be provided to enclose the diaper 10, waste containment bag 36 and rigid rib 16 for aesthetic purposes. Outer covering 42 may be provided as an integral part of diaper 10, forming an outer envelope in which are contained bag 36 and rigid rib 16, or may be provided as a separate item, to be worn over the diaper, bag and rib arrangement.

Figure 11:
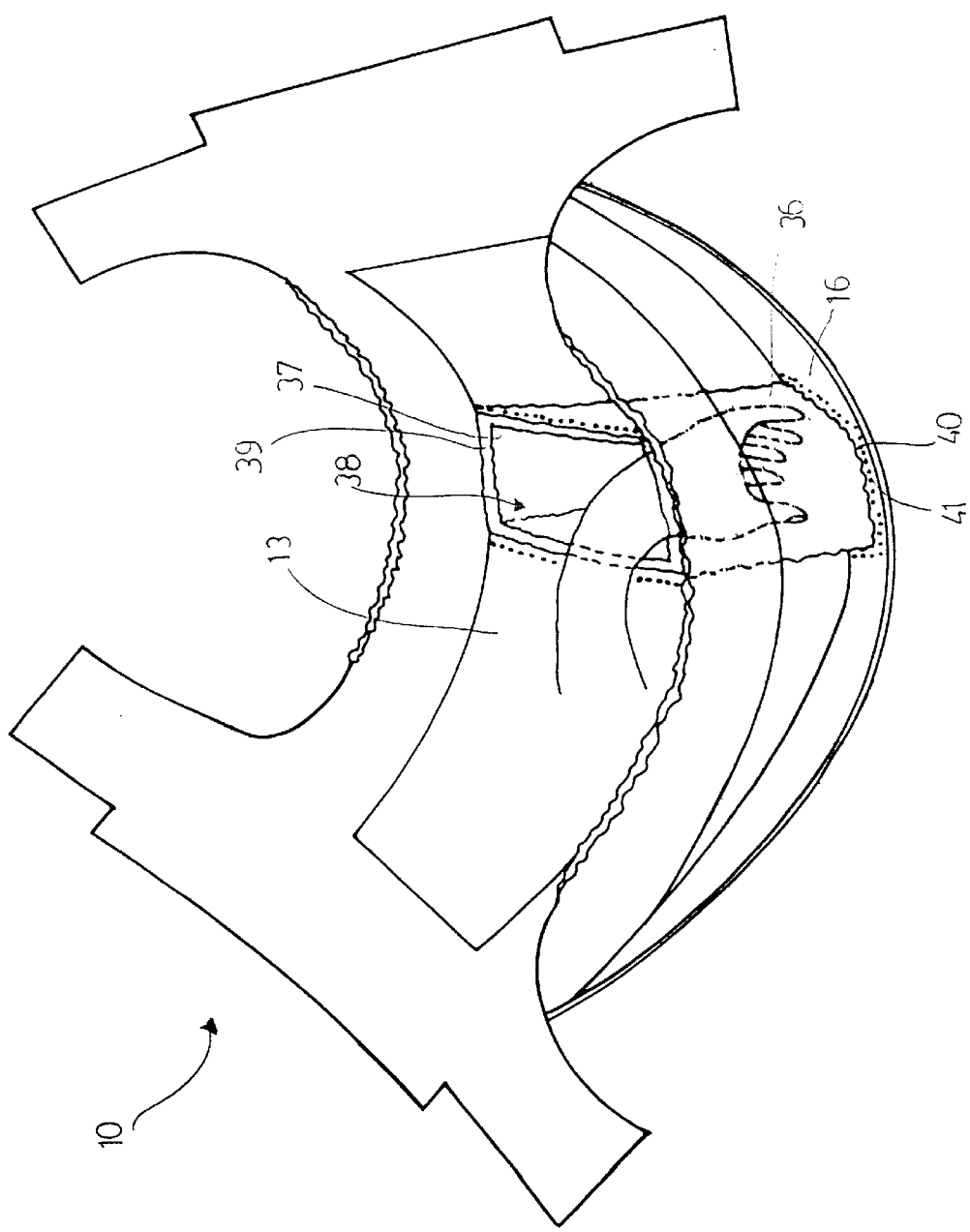
FIG. 11 shows a side perspective view of the alternative embodiment of FIG. 9, illustrating the method of insertion of the waste containment bag.

FIG. 11 shows insertion of bag 36 into aperture 38 in crotch area 13 of diaper 10. Bag 36 may be placed over the hand and inserted through aperture 38 formed in crotch area 13 of diaper 10, such that the sides 37 of the open end of bag 36 are brought into proximity to the upper edge of hole 38. Then the sides 37 of the open end of bag 36 are pressed firmly against the adhesive area 39. The lower end 40 of bag 36 is then pressed firmly against the adhesive area 41 provided on rib 16.

Figure 12:
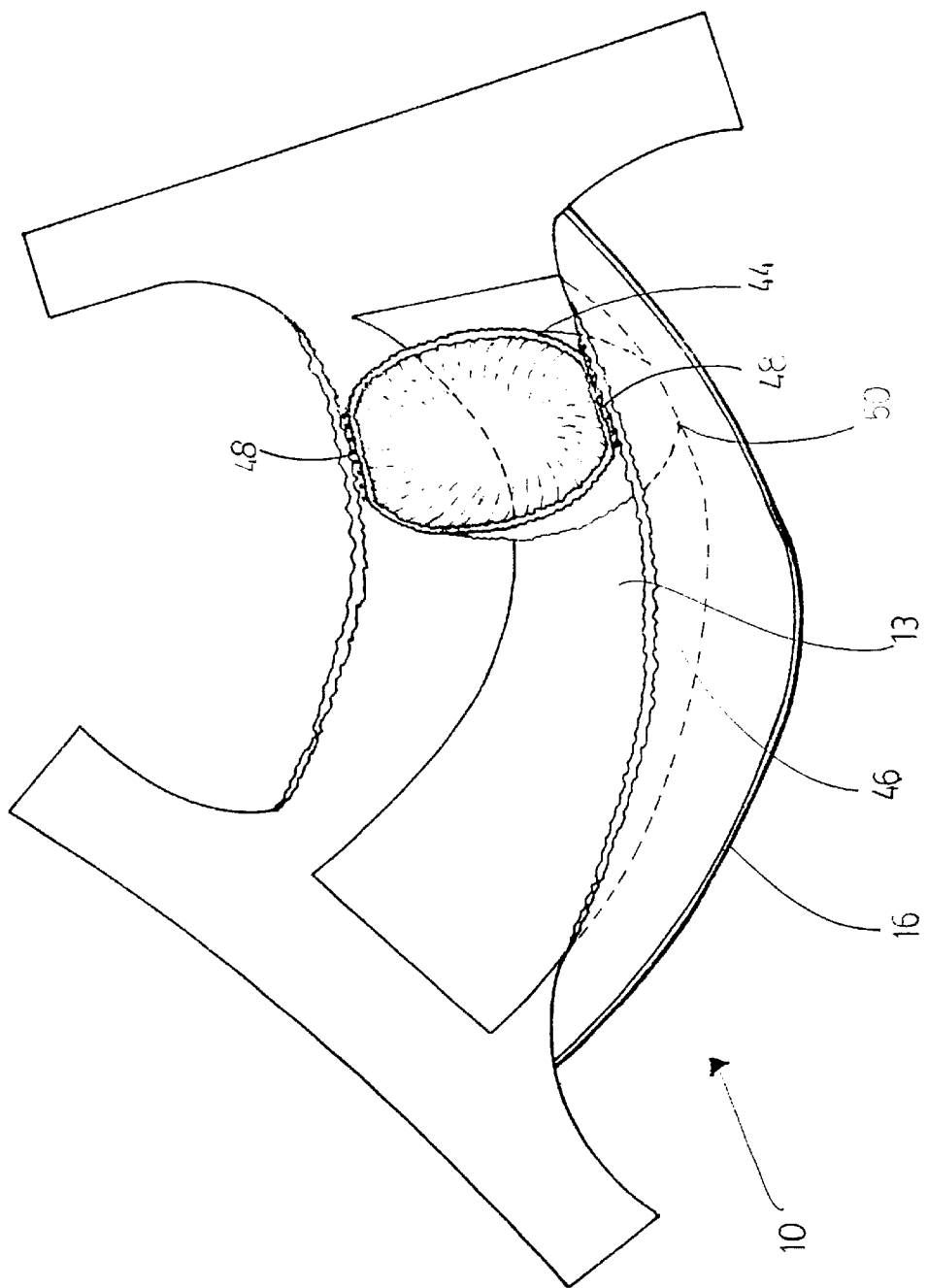
FIG. 12 shows a side perspective view of an alternative embodiment of the present invention in which a waste containment bag is provided within the crotch area.
Figure 13:
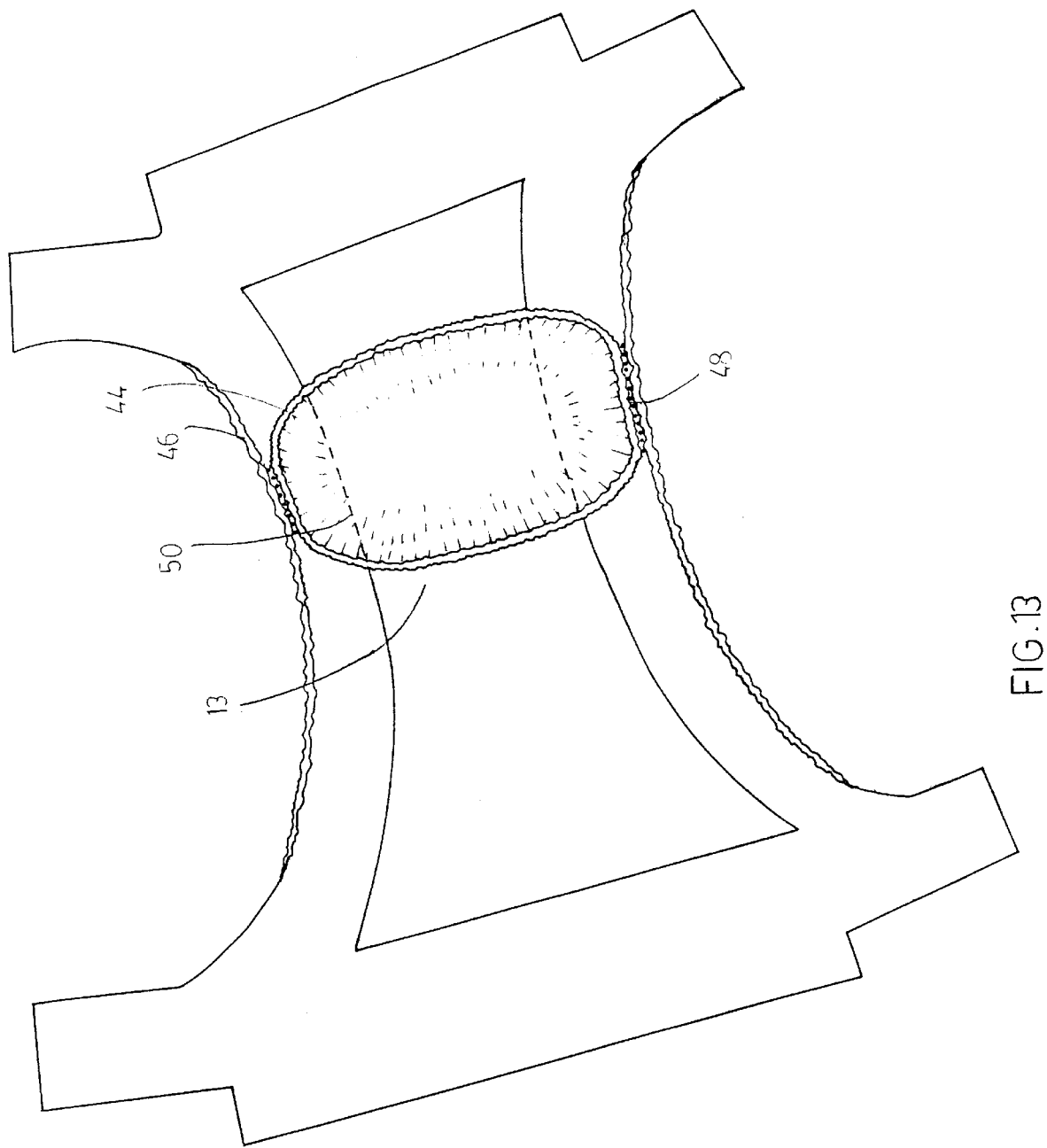
FIG. 13 shows a top view of the embodiment of FIG. 12.

FIGS. 12 and 13 show an additional preferred embodiment of the present invention in which a disposable solid waste containment bag 44 is provided to the rear of crotch area 13 of diaper 10. The sides 46 of area 13 are of greater length than those of a conventional diaper in order to accommodate the length of bag 44. The sides of the open end of bag 44 are attached at adhesive points 48 to the sides of the crotch area 13 and may be held in place, by way of example, using Velcro. Rigid rib 16, which runs along the outer surface of the crotch area 13, maintains the elongated shape of the diaper 10 in which a gap is developed between the infant's skin and the surface of crotch area 13 of the diaper 10. Bag 44 is retained within this gap. The lower surface 50 of bag 44 may be attached to the surface of crotch area 13 to prevent twisting of bag 44. When the infant assumes a seated position, waste containment bag 44 becomes folded in such a way as to contain the waste.

Thus, the anti-irritant diaper construction provides a disposable diaper which prevents solid waste from coming in contact with the skin of the infant and distances the surface of the wet absorbent material from the skin of the infant, removing the two major sources of irritation provided by prior art disposable diapers. Furthermore, because the solid waste is contained, the diaper changing process is made easier, because the area is kept cleaner.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

I claim:

1. An anti-irritant disposable diaper comprising:
   a diaper element having an interior, a front portion, a crotch area, a rear portion and closing means;
   a substantially rigid element extending from a top front edge of said diaper element, along said crotch area, to a top rear edge of said diaper element, said substantially rigid element maintaining a gap between said diaper element and a skin surface; and
   a solid waste containment means retained in said gap, such that said rigid element maintains said gap and prevents said solid waste containment means from becoming twisted and displaced.

2. The diaper of claim 1 wherein said solid waste containment means comprises:
   at least two straps each attached at one end to said crotch area, each having strap attachment means at the other end for removable attachment to a point on said top rear edge of said diaper element; and
   a solid waste containment bag for maintaining solid waste apart from said skin surface, said bag comprised of a flexible cover sealingly attached to a receptacle, said cover having formed therein an opening for receiving said solid waste therethrough, and having formed thereon attachment means enabling removable attachment to said straps, said gap being maintained by said substantially rigid element enclosing said solid waste containment bag.

3. The diaper of claim 1 wherein said rigid element is provided with a region of lower rigidity in said crotch area of said diaper element, causing said diaper element to compress when the wearer assumes a seated position, and wherein said solid waste containment means comprises a flexible flap for covering solid waste when the wearer is in a seated position.

4. The diaper of claim 1 wherein said rigid element is formed with a rigid pocket in said crotch area of said diaper element, providing space for containment of solid waste, said rigid element having a width greater than said rigid pocket so as to provide substantially flat edges for supporting an infant seated thereon.

5. The diaper of claim 1 wherein said crotch area has extended sides to ensure proper sealing of said diaper element with said gap.

6. The diaper of claim 2 wherein said cover attachment means are provided as at least two adhesive strips.

7. The diaper of claim 1 further comprising rigid element attachment means for removable attachment of said rigid element.

8. The diaper of claim 7 wherein said rigid element attachment means is provided as a sleeve in a side of said diaper element for insertion of said rigid element.

9. The diaper of claim 7 wherein said rigid element attachment means is provided as re-openable snaps on said diaper element for attachment of said rigid element.

10. The diaper of claim 1 wherein said rigid element is integrally formed with said diaper element.

11. The diaper of claim 1 wherein said rigid element is approximately 4.5 cm in width.

12. The diaper of claim 1 wherein said gap is approximately 5 cm between said diaper element and said skin surface.

13. The diaper of claim 1 further provided with a removable pad for placement between said diaper element front portion and said skin surface so as to absorb excess liquid waste.

14. The diaper of claim 2, wherein said receptacle further comprises receptacle attachment means for attaching said receptacle to said diaper element crotch area.

15. An anti-irritant disposable diaper comprising:

a diaper element having a front portion, a crotch area, a rear portion, and closing mean; and a substantially rigid element extending from a top front edge of said diaper element, along said crotch area, to a top rear edge of said diaper element, said substantially rigid element maintaining a gap between said diaper element and a skin surface to reduce irritation of said skin surface caused by waste material deposited in said diaper element.

16. An anti-irritant disposable diaper comprising:

a diaper element having a front portion, a crotch area, a rear portion, and closing means;

a substantially rigid element extending from a top front edge of said diaper element, beneath said crotch area, to a top rear edge of said diaper element; and a solid waste containment bag for maintaining solid waste apart from a skin surface, the upper end of said bag defining an opening coincident with and attachable to an aperture formed in said diaper element crotch area, the lower end of said bag being attachable to said substantially rigid element, said substantially rigid element maintaining a gap between said diaper element and a skin surface and preventing said bag from becoming twisted and displaced.

17. The diaper of claim 16 wherein said solid waste containment bag is attachable to said aperture via an adhesive area along the perimeter of said aperture.

18. The diaper of claim 16 wherein said rigid element has a contour, said diaper element being provided with an outer covering comprising a front portion, a crotch area, a rear portion and closing means, said crotch area of said covering approximating said contour of said substantially rigid element.

19. The diaper of claim 18 wherein said covering is provided as an integral part of said diaper element.

20. The diaper of claim 18 wherein said covering is provided as a separate cover.

21. The diaper of claim 1 wherein said solid waste containment means comprises a solid waste containment bag for maintaining solid waste apart from a skin surface, and having formed thereon attachment means enabling removable attachment of said bag to sides of said diaper element crotch area.

* * * * *